United States Patent [19]

Herbstman

[11] Patent Number: 5,286,266
[45] Date of Patent: Feb. 15, 1994

[54] MOTOR FUEL DETERGENT ADDITIVES - ASYMMETRICAL UREAS OF HYDROCARBYLOXYPOLYETHER AMINES AND TERTIARY AMINOALKYL PRIMARY AMINES

[75] Inventor: Sheldon Herbstman, New City, N.Y.

[73] Assignee: Texaco, Inc., White Plains, N.Y.

[21] Appl. No.: 910,912

[22] Filed: Jul. 9, 1992

[51] Int. Cl.⁵ .................... C10L 1/22; C07C 273/18
[52] U.S. Cl. .......................... 44/417; 44/334;
  44/419; 564/47; 564/59; 564/60; 564/61
[58] Field of Search ............ 44/417, 334, 418, 419;
  564/47, 59, 60, 61

[56] References Cited

U.S. PATENT DOCUMENTS

| | | |
|---|---|---|
| 3,677,726 | 7/1972 | Coram et al. |
| 3,717,447 | 2/1973 | Badin . |
| 3,981,913 | 9/1976 | Markiewitz ........................ 564/60 |
| 4,416,669 | 11/1983 | Graiff et al. ........................ 44/417 |
| 4,435,187 | 3/1984 | Graiff et al. ........................ 44/333 |
| 4,666,529 | 5/1987 | Graiff ................................ 134/20 |
| 5,024,678 | 6/1991 | Mertens-Gottselig et al. ...... 44/417 |

FOREIGN PATENT DOCUMENTS 1499411  2/1978  United Kingdom .

Primary Examiner—Prince Willis, Jr.
Assistant Examiner—Alan D. Diamond
Attorney, Agent, or Firm—James J. O'Loughlin; Christopher Nicastri

[57] ABSTRACT

The present invention provides a novel class of compounds, useful as gasoline detergent additives, comprising asymmetrical ureas of either a hydrocarbyloxypolyether amine alone, or a hydrocarbyloxypolyether amine and a tertiary aminoalkyl primary amine. The present invention also provides a motor fuel composition containing the novel asymmetrical ureas and further provides a method of synthesizing the asymmetrical ureas of the present invention.

32 Claims, No Drawings

MOTOR FUEL DETERGENT ADDITIVES - ASYMMETRICAL UREAS OF HYDROCARBYLOXYPOLYETHER AMINES AND TERTIARY AMINOALKYL PRIMARY AMINES

BACKGROUND OF THE INVENTION

1. Field of the Invention

This invention is related to gasoline engine cleaners and detergents, and more particularly to gasoline intake valve deposit (IVD) inhibitor additives, i.e., agents which assist in preventing and removing deposits from intake valves and related parts of a gasoline combustion engine. This invention also relates to combustion chamber deposit inhibitors, which reduce combustion chamber deposits, resulting in lower octane requirement increase and lower $NO_x$ emissions.

2. Description of Related Information

Combustion of a hydrocarbon motor fuel in an internal combustion engine generally results in the formation and accumulation of deposits on various parts of the combustion chamber as well as in the fuel intake and on the exhaust systems of the engine. The presence of deposits in the combustion chamber seriously reduces the operating efficiency of the engine. First, deposit accumulation within the combustion chamber inhibits heat transfer between the chamber and the engine cooling system. This leads to higher temperatures within the combustion chamber, resulting in increases in the end gas temperature of the incoming charge. Consequently, end gas auto-ignition occurs causing engine knock. In addition, the accumulation of deposits within the combustion chamber reduces the volume of the combustion zone, causing a higher than design compression ratio in the engine. This, in turn, can also lead to engine knocking. A knocking engine does not effectively utilize the energy of combustion. Moreover, a prolonged period of engine knocking can cause stress fatigue and wear in pistons, connecting rods, bearings and cam rods of the engine. The phenomenon noted is characteristic of gasoline powered internal combustion engines. It may be overcome by employing a higher octane gasoline which resists knocking for powering the engine. This need for a higher octane gasoline as mileage accumulates has become known as the engine octane requirement increase (ORI) phenomenon. It is particularly advantageous if engine ORI can be substantially reduced or eliminated by preventing or modifying deposit formation in the combustion chambers of the engine.

Another problem common to internal combustion engines is the formation of intake valve deposits, which is an especially serious problem. Intake valve deposits interfere with valve closing and eventually result in poor fuel economy. Such deposits interfere with valve motion and valve sealing, cause valve sticking, and, in addition, reduce volumetric efficiency of the engine and limit maximum power. Valve deposits are produced from the combustion of thermally and oxidatively unstable fuel or lubricating oil oxidation products. The hard carbonaceous deposits produced collect in the tubes and runners that are part of the exhaust gas recirculation (EGR) flow. These deposits are believed to be formed from exhaust particles which are subjected to rapid cooling while mixing with the air-fuel mixture. Reduced EGR flow can result in engine knock and in increased $NO_x$ emissions. It would therefore be desirable to provide a motor fuel composition which minimizes or overcomes the formation of intake valve deposits and subsequent valve sticking problems.

There are additives on the market which assist in the removal of deposits, particularly on the intake valves, such as OGA-472 ™, a product of the Oronite Co. of Wilmington, Del. These additives lack sufficient deposit cleanup activity, however, and their efficacy can be improved upon. In addition, polyisobutylene (PIB) based detergents tend to cause octane requirement increase.

Thus, it is an object of the present invention to provide a gasoline additive which will effectively remove deposits from, and prevent the formation of deposits on, the intake valves of a gasoline spark ignition engine. It is another object of the present invention to provide a gasoline additive which will perform this function while simultaneously preventing the buildup of combustion chamber deposits.

SUMMARY OF THE INVENTION

The present invention provides a novel class of compounds, useful as gasoline detergent additives, comprising asymmetrical ureas of either a hydrocarbyloxypolyether amine alone, or a hydrocarbyloxypolyether amine and a tertiary aminoalkyl primary amine. These novel asymmetrical ureas can be represented by the formula of FIG. 1:

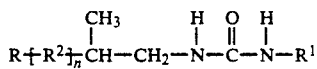

FIG. 1 where R is a $C_{12}$–$C_{24}$ alkylphenoxy or di-alkylphenoxy group or a $C_9$–$C_{24}$ alkyloxy group, $R^1$ is hydrogen or a $C_5$–$C_{20}$ tertiary aminoalkyl group, $R^2$ is a $C_2$ to $C_4$ oxyalkylene group and n is a number between about 5 and about 20.

The present invention also provides a motor fuel composition comprising:
(a) a major portion of a hydrocarbon fuel boiling in the range between 90° F. and 370° F.; and
(b) a minor amount, sufficient to reduce the formation of deposits on intake valves, of the asymmetrical urea of FIG. 1.

A method of synthesizing the asymmetrical ureas of the present invention is also provided.

DETAILED DESCRIPTION OF THE INVENTION

Applicant has discovered a new class of asymmetrical ureas which are useful as detergents in motor fuel compositions. These asymmetrical urea detergents are more efficacious in removing and preventing the build up of deposits on intake valves than some commercially available detergent packages. In addition, the asymmetrical urea motor fuel additives of the present invention will not contribute significantly, if at all, to octane requirement increase, a problem which confronts all gasoline spark ignition engines.

The asymmetrical ureas of the present invention are represented by the formula of FIG. 2:

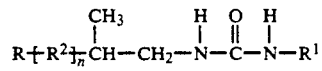

FIG. 2 where R is a $C_{12}$–$C_{24}$ alkylphenoxy or di-alkylphenoxy group or a $C_9$–$C_{24}$ alkyloxy group, $R^1$ is hydrogen or a $C_5-C_{20}$ tertiary aminoalkyl group, $R^2$ is a $C_2$ to $C_4$ oxyalkylene group and n is a number between about 5 and about 20.

Preferably, R is a $C_{15}$ to $C_{18}$ alkylphenoxy or di-alkylphenoxy group or a $C_{16}-C_{18}$ alkyloxy group, $R^1$ is a $C_5-C_{14}$ tertiary aminoalkyl group, $R^2$ is an oxypropylene group and n is a number between about 9 and about 15.

Most preferably, R is a nonylphenoxy group, $R^1$ is a tertiary aminoalkyl group represented by the formula

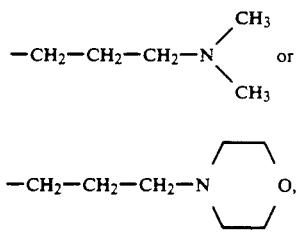

$R^2$ is an oxypropylene group, and n is about 12.5.

The most preferred asymmetrical ureas of the present invention can be represented by the following formulas in FIG. 3 and FIG. 4:

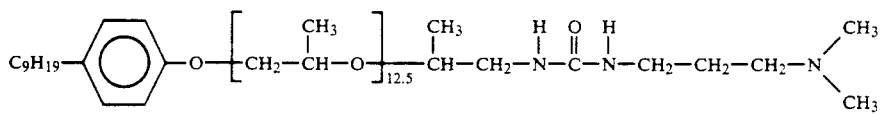

Asymmetrical N,N-Dimethylaminopropylamine-nonylphenoxypolyoxypropylene Urea
FIG. 3

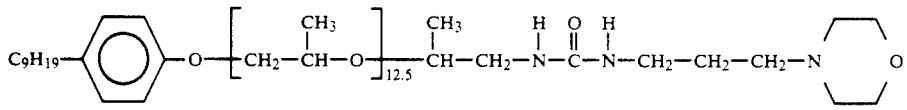

Asymmetrical Aminopropylmorpholine-nonylphenoxypolyoxypropylene Urea
FIG. 4

It should be noted that the phenyl ring of each compound can contain a second nonyl substituent.

Synthesis of Asymmetrical Ureas

In general, the asymmetrical ureas of the present invention are synthesized by reacting a polyether amine with urea, and then optionally reacting the product of this reaction with a tertiary aminoalkyl primary amine. Alternatively, the tertiary aminoalkyl primary amine can be reacted with urea first, and the product of that reaction can then be reacted with the polyether amine. In addition, all three reactants can be reacted simultaneously.

The Polyetheramine Reactant

The polyetheramine reactant can be represented by the formula of FIG. 5:

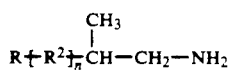

FIG. 5 where R is a $C_{12}-C_{24}$ alkylphenoxy or di-alkylphenoxy group or a $C_9-C_{24}$ alkyloxy group, $R^2$ is a $C_2$ to $C_4$ oxyalkylene group and n is a number between about 5 and about 20.

Preferably, R is a $C_{15}$ to $C_{18}$ alkylphenoxy or di-alkylphenoxy group or a $C_{16}-C_{18}$, alkyloxy group, $R^2$ is an oxypropylene group and n is a number between about 9 and about 15.

The most preferred polyetheramine, nonylphenoxypolyoxypropyleneamine, can be represented by the formula in FIG. 6 below:

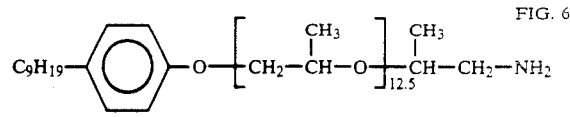

FIG. 6

Nonylphenoxypolyoxypropyleneamine is available from Texaco Chemical Company. It should be noted that the preferred polyetheramine can have two nonyl groups substituted onto the phenyl ring. In fact, it is likely that commercially available nonylphenoxypolyoxypropyleneamine contains at least some of the dinonyl substituted phenyl ring versions of this compound.

The Tertiary Aminoalkyl Primary Amine Reactant

The tertiary aminoalkyl primary amines useful in the present invention can be represented by the formula $H_2N-R^1$, where $R^1$ is a $C_5-C_{20}$ tertiary aminoalkyl group.

Preferred tertiary aminoalkyl primary amines can be represented by the formula of FIG. 7:

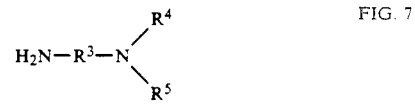

FIG. 7 where $R^3$ is a $C_3-C_{10}$ alkylene group, and $R^4$ and $R^5$ are the same or different $C_1-C_5$ alkyl groups.

For example, the following tertiary aminoalkyl primary amines, available from Aldrich Chemical Company, are useful in the present invention:
N-ethyl-N-methylethylene diamine;
N,N-dimethylethylene diamine;
1-N,N-diethyl-1,3-propane diamine; and
1-N-methyl-N-ethyl-1,3-propane diamine.

The most preferred tertiary aminoalkyl primary amines useful in the present invention, dimethylaminopropylamine (DMAPA) and aminopropylmorpholine (APM), can be represented by the formulas in FIG. 8 and FIG. 9, respectively:

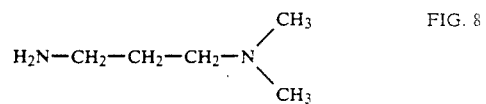

FIG. 8

-continued

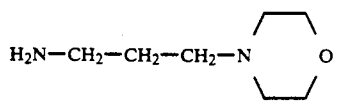

FIG. 9

DMAPA and APM are available from the Texaco Chemical Company.

The Synthesis

The asymmetrical ureas of the present invention can be prepared via the following "two-step" reaction. In step one, as shown in Equation I, a polyetheramine is heated with urea at a temperature of about 130° C. for about 6-15, and preferably 8, hours with stirring, under a nitrogen sparge to remove the evolved ammonia.

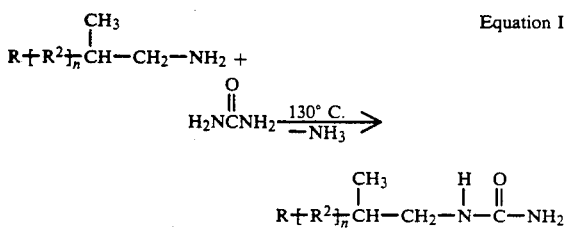

Equation I

In Equation I, R, R$^2$ and n are defined as above for the polyether amine reactant.

After cooling, the mixture is filtered free of unreacted urea. The product is a polyether urea, i.e., the mono-substituted asymmetrical urea of the present invention. This asymmetrical urea is useful in this form, and can also be further processed in a second step to provide the di-substituted asymmetrical ureas of the present invention.

In step two, as shown in Equation II, the product of Equation I is reacted with a tertiary aminoalkyl primary amine at a temperature of about 130° C. for about 6-15 (and preferably about 8) hours with stirring, under a nitrogen sparge to remove the evolved ammonia. After cooling, the reaction mixture is filtered free of unreacted reactants, and stripped under vacuum at about 80° C. for about an hour. The product is a di-substituted asymmetrical urea of the present invention.

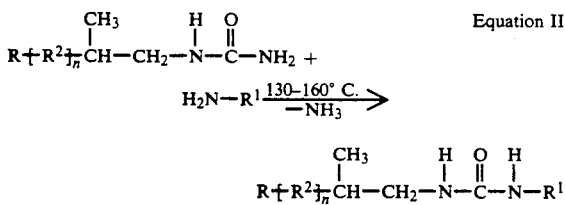

Equation II

In Equation II, R, R$^1$, R$^2$ and n are defined as above for the polyether amine and tertiary aminoalkyl primary amine reactants.

The two step synthesis can also be performed in reverse order, i.e., the tertiary aminoalkyl primary amine is reacted with urea in the first step and the product of this first reaction is then reacted with the polyether amine in the second step.

Alternatively, the di-substituted asymmetrical ureas of the present invention can be prepared via a "one-step" reaction. The polyether amine, urea and tertiary aminoalkyl primary amine are charged into a vessel and reacted at about 130°-160° C. for about 6-15 (and preferably about 8) hours. The reaction is conducted under a nitrogen sparge to remove evolved ammonia, followed by filtering of unreacted reactants and stripping under a vacuum at about 80° C. for about an hour.

All of the reactions described above can be conducted in solution in hydrocarbon type heavy oils (e.g., SNO-600, SNO-850, etc.) it is also possible to use a slight excess of the tertiary aminoalkyl primary amine (about 5%) which can be stripped off at the end of the reactions.

The Motor Fuel Composition

The motor fuel composition of the present invention comprises a major portion of a hydrocarbon fuel boiling in the gasoline range between 90° F. and about 370° F., and a minor portion of the asymmetrical urea additive of the present invention sufficient to reduce the formation of deposits on intake valves.

Preferred base motor fuel compositions are those intended for use in spark ignition internal combustion engines. Such motor fuel compositions, generally referred to as gasoline base stocks, preferably comprise a mixture of hydrocarbons boiling in the gasoline boiling range, preferably from about 90° F. to about 370° F. This base fuel may consist of straight chain or branched chain paraffins, cycloparaffins, olefins, aromatic hydrocarbons, or mixtures thereof. The base fuel can be derived from, among others, straight run naphtha, polymer gasoline, natural gasoline, or from catalytically cracked or thermally cracked hydrocarbons and catalytically reformed stock. The composition and octane level of the base fuel are not critical and any conventional motor fuel base can be employed in the practice of this invention. In addition, the motor fuel composition may contain any of the additives generally employed in gasoline. Thus, the fuel composition can contain anti-knock compounds such as tetraethyl lead compounds, anti-icing additives, and the like.

In a broad embodiment of the fuel composition of the present invention, the concentration of the additive is about 25 to about 360 PTB (pounds per thousand barrels of gasoline base stock). In a preferred embodiment, the concentration of the additive composition is about 25 to about 250 PTB. In a more preferred embodiment, the concentration of the additive composition is about 50-125 PTB.

The additive of the present invention can also be used effectively with heavy oils such as SNO-600, SNO-850, etc., or with synthetics such as polypropylene glycol (1000 m.w.) at concentrations of 25-400 PTB, and 100 PTB in particular.

The additive of the present invention is effective in very small concentrations and, therefore, for consumer end use it is desirable to package it in dilute form. Thus, a dilute form of the additive composition of the present invention can be provided comprising a diluent e.g., xylene and about 1 to about 50 wt. % of the additive.

The preparation and advantages of the asymmetrical ureas of the present invention are further illustrated by the following examples.

EXAMPLE 1

Synthesis of Polyether Urea 100 grams of nonylphenoxypolyoxypropyleneamine (FIG. 6, above) were heated with 7.0 grams of urea with stirring at 130° C. for 8 hours under a nitrogen sparge to remove ammonia. After cooling, the reaction mixture was filtered free of unreacted urea. Yield of polyether urea was 95%, based upon nitrogen and total base number (TBN) analysis.

Analysis: N (wt. %)=2.40%. Check=2.47% (Theory=2.9%). Infrared analysis (FTIR) indicates urea absorptions (C=O) at 1560, 1610, 1660 and 1690 cm$^{-1}$.

EXAMPLE 2

Synthesis of Asymmetrical N,N-Dimethylaminopropylamine-polyetheramine Urea 100 grams of nonylphenoxypolyoxypropyleneamine (FIG. 6, above) and 7 grams of urea were introduced to a reaction vessel with a nitrogen sparger and heated at 130° C. for 4 hours. 11.0 grams of N,N-dimethylaminopropylamine (DMAPA) were introduced over 1 hour at 130° C. and the reaction was heated an additional 3 hours. After cooling, the reaction mixture was filtered free of unreacted urea, and stripped under vacuum at about 80° C. for an additional hour. 114.8 grams of asymmetrical N,N-dimethylaminopropylamine-nonylphenoxypolyoxypropylene urea (FIG. 3 above) were recovered.

Analysis: N (wt %)=4.34. Check 4.27% (Theory=4.28%). Total Base Number (TBN)=106.

EXAMPLE 3

Synthesis of Asymmetrical Aminopropylmorpholine-polyetheramine Urea 100 grams of nonylphenoxypolyoxypropylene urea (which can be represented by the formula of FIG. 9),

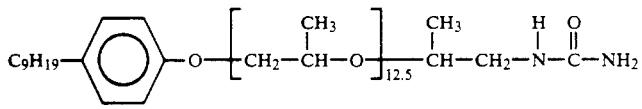

were reacted with 14 grams of aminopropylmorpholine at 130°–135° C. for 8 hours. After stripping, 105 grams of asymmetrical aminopropylmorpholine-nonylphenoxypolyoxypropylene urea (FIG. 4, above) were recovered.

Analysis: N (wt. %)=3.78. TBN=92.

EXAMPLE 4

Synthesis of Polyether Urea Using a Low Molecular Weight Polyether Amine 200 grams of low molecular weight polyetheramine (i.e., the polyether amine of FIG. 5 wherein n=6, R is a nonyloxy group and R$^2$ is an oxypropylene group) were reacted with 19.8 grams of urea at 130° C. for 8 hours. After filtering unreacted urea, 176.2 grams of low molecular weight polyether urea were recovered, for an 80% yield.

Analysis: N (wt. %)=3.03. TBN=12.85. Gel Phase Chromatography indicates a molecular weight of 1160. Nuclear Magnetic Resonance and Infrared Spectroscopy confirm structure of urea.

EXAMPLE 5

Intake Valve Keep Clean Test

The motor fuel composition of the present invention is advantageous in that it reduces intake valve deposit formation. The advantage of the instant invention in controlling intake valve deposit formation has been shown by the comparison of the performance of motor fuel compositions of the present invention and a motor fuel containing a commercially available detergent package.

The following fuel compositions, identified in Table II, were subjected to Honda Generator-IVD "Keep Clean" testing. The base fuel used in each fuel composition was a commercial unleaded fuel with 45% aromatics, 6% olefins, and the remainder paraffins. The octane rating, calculated as the average of research and motor octane ratings was 87. Base fuel boiling point data is listed in Table I as follows:

TABLE I

| | |
|---|---|
| initial boiling point | 37° C. |
| 50% point | 123° C. |
| 90% point | 210° C. |
| end point | 213° C. |

Fuel A contained 100 PTB of a mono-substituted asymmetrical urea of the present invention as a detergent additive and 100 PTB of heavy oil, Fuels B and C contained 100 PTB of a di-substituted asymmetrical urea of the present invention as a detergent additive and 100 PTB of heavy oil, and Fuel D, contained 60 PTB of a commercially available gasoline additive package.

TABLE II

| Fuel | | Additive |
|---|---|---|
| A | Product of Example 1 - | nonylphenoxypolyether urea |
| B | Product of Example 3 - | asymmetrical aminopropyl-morpholine-nonylphenoxypoly-oxypropylene urea |
| C | Product of Example 2 - | asymmetrical N,N-dimethyl-aminopropyl-nonylphenoxypolyether urea |

FIG. 9

The Honda Generator Test employed a Honda ES6500 generator with the following specifications:

TABLE III

| Honda ES6500 Generator | |
|---|---|
| Type: | 4-stroke, overhead cam, 2-cylinder |
| Cooling system: | Liquid-cooled |
| Displacement: | 369 cubic cm. (21.9 cu. in) |
| Bore × stroke: | 58 × 68 mm (2.3 × 2.7 in) |
| Maximum Horsepower: | 12.2 HP/3600 rpm |
| Maximum Torque: | 240 kg-cm (17.3 ft-lb)/3000 rpm |

Each generator was equipped with an auto-throttle controller to maintain the rated speed when load was applied. Load was applied to each generator by plugging in a water heater. Various loads were simulated by changing the size of the water heaters connected to the generator.

The procedure for the Honda Generator Test is as follows. The test was started with a new or clean engine (clean valve, manifold, cylinder head, combustion chamber) and a new charge of lubricant. The generator was operated for 80 hours on the fuel to be tested following the test cycle of 2 hours at 1500 Watt load and 2 hours at 2500 Watt load, both at 3600 r.p.m. The engine was thereafter disassembled and the cylinder head stored, with valve spring and seal removed, in a freezer overnight at 0° F.

IV Stickiness Test

A trained rater quantified the effort to push open the intake valves by hand. The amount of effort was correlated to valve sticking problems in vehicles: i.e., valves that could not be pushed open by hand generally correlated with cold starting problems in vehicles.

CRC IV Test

The intake system components (valve, manifold, cylinder head) and combustion chamber were rated visually according to standard Coordinating Research Council (CRC) procedures (scale from 1-10: 1=dirty; 10=clean). The performance of the test fuel was measured in part by the cleanliness of the intake system components.

Each fuel listed in Table II was subjected to the Honda Generator intake valve keep clean test procedure. The results are summarized in Table IV:

TABLE IV

| FUEL | CRC IV | Wt., mg., IV | IV Stickiness |
|---|---|---|---|
| A | 8.65 | 0.005 | No |
| B | 9.1 | 0.005 | No |
| C | 9.5 | 0.008 | No |
| D | 6.03 | 0.269 | No |

The additive gasolines of the present invention, i.e., Fuels A, B and C, demonstrated excellent CRC valve ratings, virtually no deposits on the intake valves (8 mg or less) and exhibited no stickiness. The fuel containing the commercially available additive package showed a poor CRC rating and gave 269 mg intake valve deposits. Therefore the asymmetrical ureas of the present invention demonstrate excellent detergency and intake valve detergency keep clean properties.

EXAMPLE 6

Thermal Gravimetric Analysis (TGA)

Samples of the asymmetrical ureas were analyzed for rate of thermal decomposition using TGA analysis, in order to determine whether they will increase combustion chamber deposits. The procedure used was the Chevron test method, which involves heating the additive compound in air at a rapid rate and measuring its volatility at 200° C. and 295° C. The test method is more specifically described as follows:

The sample is heated to 200° C., kept at this temperature for 30 minutes, and then heated to 295° C., where it is kept for an additional 30 minutes. The weight of the sample, (initially about 20 mg) is recorded at the start, after the first heating period and after the final heating period. The difference in weights from the start to 200° C., and from 200° C. to 295° C. is recorded and the percent loss, i.e., volatility, is calculated. (The final weight at 295° C. is also considered residue.) The heating is done under a flow of air at 60 cc/min.

The following results were obtained:

TABLE V

| Run | Additive | % Volatilized (in Air) 200° C. | % Volatilized (in Air) 295° C. | Residue (wt. %) 295° C. |
|---|---|---|---|---|
| 1 | Product of Example 1 - nonylphenoxypolyoxypropylene urea | 24.7 | 94 | 6 |
| 2 | Product of Example 2 - asymmetrical N,N-dimethyl-aminopropylamine-nonylphenoxypolyoxypropylene urea | 14.0 | 90 | 10 |
| 3 | Product of Example 3 - asymmetrical aminopropyl-morpholine-nonylphenoxypolyoxypropylene urea | 38.0 | 95 | 5 |
| 4 | OGA-472 ™ | 34.5 | 62.8 | 37.2 |

The test results for runs 1, 2, 3, and 4 show that at 295° C., 90-95% of the additives of the present invention had thermally decomposed and volatilized, compared to only 62.8% for a PIB containing derivative such as OGA-472 ™. These results indicate that the additives of the present invention should leave only small amounts of combustion chamber deposits during the actual engine operation, and therefore will not contribute to octane requirement increase.

I claim:

1. An asymmetrical urea comprising a compound of formula

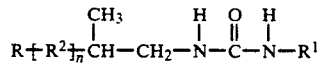

where R is a $C_{12}$-$C_{24}$ alkylphenoxy or di-alkylphenoxy group, $R^1$ is hydrogen or a $C_5$-$C_{20}$ tertiary aminoalkyl group, $R^2$ is a $C_2$ to $C_4$ oxyalkylene group and n is a number between about 5 and about 20.

2. The asymmetrical urea of claim 1 where R is a $C_{14}$ to $C_{20}$ alkylphenoxy or di-alkylphenoxy group.

3. The asymmetrical urea of claim 1 where $R^2$ is an oxypropylene group.

4. The asymmetrical urea of claim 1 where n is a number between about 9 and about 15.

5. The asymmetrical urea of claim 1 where $R^1$ is a tertiary aminoalkyl group represented by the formula

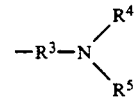

where $R^3$ is a $C_3$-$C_{10}$ alkylene group, and $R^4$ and $R^5$ are the same or different $C_1$-$C_5$ alkyl groups.

6. The asymmetrical urea of claim 1 where $R^1$ is a tertiary aminoalkyl group represented by the formula

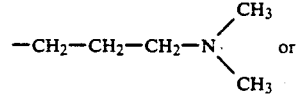

or

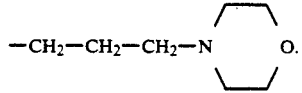

7. The asymmetrical urea of claim 1 where
R is a nonylphenoxy group;
$R^1$ is hydrogen or a tertiary aminoalkyl group represented by the formula

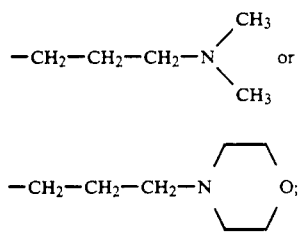

$R^2$ is an oxypropylene group; and
n is about 12.5.

8. An asymmetrical urea comprising a compound of formula

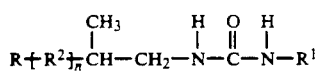

where R is a $C_{12}$-$C_{24}$ alkylphenoxy or di-alkylphenoxy group or a $C_9$-$C_{24}$ alkyloxy group, $R^1$ is a $C_5$-$C_{20}$ tertiary aminoalkyl group, $R^2$ is a $C_2$ to $C_4$ oxyalkylene group and n is a number between about 5 and about 20.

9. The asymmetrical urea of claim 8 where R is a $C_{14}$ to $C_{20}$ alkylphenoxy or di-alkylphenoxy group.

10. The asymmetrical urea of claim 8 where R is a $C_{16}$ to $C_{18}$ alkyloxy group.

11. The asymmetrical urea of claim 8 where $R^2$ is an oxypropylene group.

12. The asymmetrical urea of claim 8 where n is a number between about 9 and about 15.

13. The asymmetrical urea of claim 8 where $R^1$ is a tertiary aminoalkyl group represented by the formula

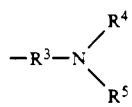

where $R^3$ is a $C_3$-$C_{10}$ alkylene group, and $R^4$ and $R^5$ are the same or different $C_1$-$C_5$ alkyl groups.

14. The asymmetrical urea of claim 8 where $R^1$ is a tertiary aminoalkyl group represented by the formula

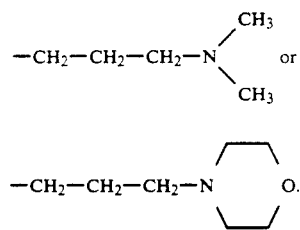

15. A motor fuel composition comprising:
a) a major portion of a hydrocarbon fuel boiling in the range between 90° F. and 370° F.; and
b) a minor amount, sufficient to reduce the formation of deposits on intake valves, of an asymmetrical urea comprising a compound of formula

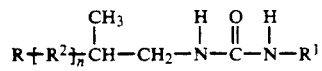

where R is a $C_{12}$-$C_{24}$ alkylphenoxy or di-alkylphenoxy group, $R^1$ is hydrogen or a $C_5$-$C_{20}$ tertiary aminoalkyl group, $R^2$ is a $C_2$ to $C_4$ oxyalkylene group and n is a number between about 5 and about 20.

16. The motor fuel composition of claim 15 where R is a $C_{14}$ to $C_{20}$ alkylphenoxy or di-alkylphenoxy group.

17. The motor fuel composition of claim 15 where $R^2$ is an oxypropylene group.

18. The motor fuel composition of claim 15 where n is a number between about 9 and about 15.

19. The motor fuel composition of claim 15 where $R^1$ is a tertiary aminoalkyl group represented by the formula

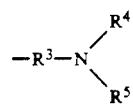

where $R^3$ is a $C_3$-$C_{10}$ alkylene group, and $R^4$ and $R^5$ are the same or different $C_1$-$C_5$ alkyl groups.

20. The motor fuel composition of claim 15 where $R^1$ is a tertiary aminoalkyl group represented by the formula

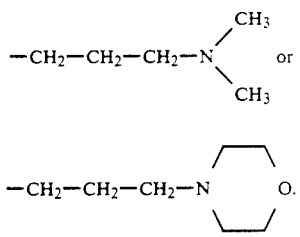

21. The motor fuel composition of claim 15 where
R is a nonylphenoxy group;
$R^1$ is hydrogen or a tertiary aminoalkyl group represented by the formula

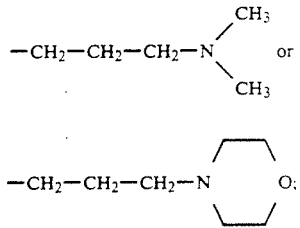

$R^2$ is an oxypropylene group; and
n is about 12.5.

22. The motor fuel composition of claim 15 wherein the asymmetrical urea is present in an amount of between about 25 and about 250 PTB.

23. The motor fuel composition of claim 15 wherein the asymmetrical urea is present in an amount of between about 50 and 125 PTB.

24. A motor fuel composition comprising:
a) a major portion of a hydrocarbon fuel boiling in the range between 90° F. and 370° F.; and
b) a minor amount, sufficient to reduce the formation of deposits on intake valves, of an asymmetrical urea comprising a compound of formula

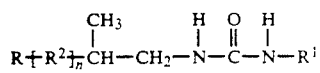

where R is a $C_{12}$-$C_{24}$ alkylphenoxy or di-alkylphenoxy group or a $C_9$-$C_{24}$ alkyloxy group, $R^1$ is a $C_5$-$C_{20}$ tertiary aminoalkyl group, $R^2$ is a $C_2$ to $C_4$ oxyalkylene group and n is a number between about 5 and about 20.

25. The motor fuel composition of claim 24 where R is a $C_{14}$ to $C_{20}$ alkylphenoxy or di-alkylphenoxy group.

26. The motor fuel composition of claim 24 where R is a $C_{16}$ to $C_{18}$ alkyloxy group.

27. The motor fuel composition of claim 24 where $R^2$ is an oxypropylene group.

28. The motor fuel composition of claim 24 where n is a number between about 9 and about 15.

29. The motor fuel composition of claim 24 where $R^1$ is a tertiary aminoalkyl group represented by the formula

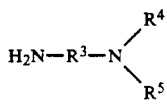

where $R^3$ is a $C_3$-$C_{10}$ alkylene group, and $R^4$ and $R^5$ are the same or different $C_1$-$C_5$ alkyl groups.

30. The motor fuel composition of claim 24 where $R^1$ is a tertiary aminoalkyl group represented by the formula

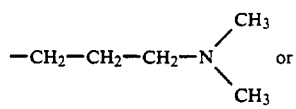 or

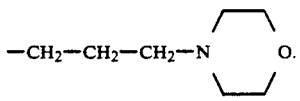

31. The motor fuel composition of claim 24 wherein the asymmetrical urea is present in an amount of between about 25 and about 250 PTB.

32. The motor fuel composition of claim 24 wherein the asymmetrical urea is present in an amount of between about 50 and 125 PTB.

* * * * *